US007172901B2

(12) United States Patent
Herrmann et al.

(10) Patent No.: US 7,172,901 B2
(45) Date of Patent: Feb. 6, 2007

(54) SCORPION TOXINS

(75) Inventors: Rafael Herrmann, Wilmington, DE (US); Jian-Ming Lee, Monroe, CT (US); Albert L. Lu, Newark, DE (US); James K. Presnail, Landenberg, PA (US); James F H Wong, Johnston, IA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 369 days.

(21) Appl. No.: 10/614,934

(22) Filed: Jul. 8, 2003

(65) Prior Publication Data

US 2005/0042717 A1 Feb. 24, 2005

Related U.S. Application Data

(62) Division of application No. 09/857,401, filed as application No. PCT/US99/28351 on Dec. 1, 1999.

(60) Provisional application No. 60/110,590, filed on Dec. 2, 1998.

(51) Int. Cl.
*C12N 15/12* (2006.01)
*C12N 15/63* (2006.01)
*C12N 5/10* (2006.01)
*C12N 1/16* (2006.01)
*C12N 1/21* (2006.01)

(52) U.S. Cl. .................. 435/440; 536/23.5; 435/320.1; 435/252.3; 435/254.11; 435/419; 435/455; 435/468; 435/471; 435/348; 435/254.2

(58) Field of Classification Search ..................... None
See application file for complete search history.

(56) References Cited

U.S. PATENT DOCUMENTS 4,925,664 A 5/1990 Jackson et al.

FOREIGN PATENT DOCUMENTS

EP 0374753 A2 12/1989
EP 0 374 753 A2 6/1990
WO WO 94/28114 A1 12/1994
WO WO 95/03065 A1 2/1995

OTHER PUBLICATIONS

Maria L. Garcia et al, Biochemistry, vol. 33:6834-6839, 1994, Purification and Characterization of Three inhibitors of Voltage-Dependent K + Channels from *Leiurus quinquestriatus* var. *hebraeus* Venom.

D.L. Marshall et al., Toxicon, vol. 32(11):1433-1443, 1994, Neuromuscular Effects of Some Potassium Channel Blocking Toxins from the Venom of the Scorpion *Leiurus quinquestriatus hebreus*.

J.M. Sabatier et al., Int. J. Peptide Protein Res., vol. 43:486-495, 1994, Leiurotoxin I, a scorpion toxin specific for Ca2+-activated K+ channels.

Elishu Zlotkin et al., Phytoparasitica, vol. 19(3):177-182, 1991, Venom Neurotoxins—Models for Selective Insecticides.

E. Zlotkin et al., Archives of Biochem. & Biophys., vol. 240(2):877-887, 1985, An Excitatory and a Depressant Insect Toxin from Scorpion Venom both Affect Sodium Conductance and Possess a Common Binding Site.

E. Zlotkin et al., Biochimie, vol. 53:1073-1078, 1971, Purification and properties of the insect toxin from the venom of the scorpion *Androctonus australis* Hector.

Mark D. Adams et al., Science, vol. 252:1651-1656, 1991, Complementary DNA Seqencing: Expressed Sequence Tags and Human Genome Project.

Garcia et al. Purification and characterization of three inhibitors of voltage-dependent K+ channels from *Leiurus quinquestriatus* var. *hebraeus* venom. 1994. Biochemistry 33: 6834-6839.

Marshall et al. Neuromuscular effects of some potassium channel blocking toxins from the venom of *Leiurus quniquestriatus hebraeus*. 1994. Toxicin 32(11): 1433-1434.

Norton et al. The cystine knot structure of ion channel toxins and related Polypeptides. Nov. 1998. Toxicon 36 (11) :1573-1583.

*Primary Examiner*—Gabriele Bugaisky

(57) ABSTRACT

This invention relates to an isolated nucleic acid fragment encoding scorpion toxins that are K-channel agonists. The invention also relates to the construction of a chimeric gene encoding all or a portion of the K-channel agonists, in sense or antisense orientation, wherein expression of the chimeric gene results in production of altered levels of the K-channel agonists in a transformed host cell.

11 Claims, 8 Drawing Sheets

Figure 1

```
                                           *      *    *          *    *  *
SEQ ID NO:17  ......................GLIDVRCYDSRQCWIACKKVTGSTQGKCQNKQCRCY
SEQ ID NO:02  MKILSVLLIAFIICSINICSEAGLIDVRCFASRECWEACRKVTGSGQGKCQNNQCRCY
              1                                                        58
```

FIGURE 2

```
                         *         *       *             *      *   *
SEQ ID NO:18  GVPINVK    C  TGSPQ  C  LKP  C  KDAGMRFGK  C  INGK  C H C  TPK
SEQ ID NO:04  FINSNVEAA  C  G PG   C  RSS  C  QQSGNSGGK  C  INGR  C H C  YPXK
              1                                                            39
```

FIGURE 3

```
                  *    *     *          *     *  *
SEQ ID NO:19  VS C ED C PDH C STQKARAK C DNDK C V C EPI
SEQ ID NO:06  VS C ED C PEH C STQKARAK C DNDK C V C ESI
              1                                    29
```

FIGURE 4

```
                              *     *   *         *    * *
SEQ ID NO:20 MKVFSAVLIILFVCSMIIGINAVRIPVSCKHSGQCLKPCKDAGMRFGKCMNGKCDCTPK
SEQ ID NO:08 MKVFFAVLITLFVCSMIIGINAVGIPVSCIHSRQCWEPCKKAGMRFGKCMNRKCDCTPK
             1                                                        59
```

FIGURE 5

```
                   *      *    *           *    * *
SEQ ID NO:21 VFINAKCRGSPECLPKCKEAIGKAAGKCMNGKCKCYP
SEQ ID NO:10 IHTNVPCKNSGQCRPVCIKRVNNNSGKCGNDKCICYP
             1                                  37
```

FIGURE 6

```
                                     *       *     *            *      *  *
SEQ ID NO:22  .............QFTNVS C TTSKE C WSV C QRLHNTSRGK C MNKK C R C YS
SEQ ID NO:12  LSSICSIVGWSEAQFTDVS C TTSKE C WSV C ETLYKTTRGK C MNWK C R C YS
              1                                                        50
```

FIGURE 7

```
                                 *      *   *          *    * *
SEQ ID NO:23   VDGSIEGRQFTNVS C TTSKE C WSV C QRLHNTSRGK C MNKK C R C YS
SEQ ID NO:14   MMIFCQGQKKINYR C NNSGE C IPH C IRIYNTRAAK C INKT C N C YP
               1                                                    45
```

FIGURE 8

```
                                            *      *    *           *     *  *
SEQ ID NO:24  ......................QFTQES C TASNQ C WSI C KRLHNTNRGK C MNKK C R C YS
SEQ ID NO:16  MKILSALLLALIICSIVGWSTAQFTQVS C SASDQ C WLV C QNLYKTLNAK C MNNK C R C YS
              1                                                                  60
```

SCORPION TOXINS

This application is a division of U.S. application Ser. No. 09/857,401, filed Jun. 1, 2001, now U. S. Pat. No. 6,593,141, which is a 371 of PCT Application PCT/US99/28351, filed Dec. 01, 1999, which claims the benefit of U.S. Provisional Application No. 60/110,590, filed Dec. 2, 1998.

FIELD OF THE INVENTION

This invention is in the field of molecular biology. More specifically, this invention pertains to nucleic acid fragments encoding scorpion toxins that are potassium channel agonists.

BACKGROUND OF THE INVENTION

Scorpion venoms have been recognized as a source of peptidyl inhibitors of various types of potassium ion (K) channels. Some of these peptides have been purified to homogeneity and their properties characterized. The most extensively studied of these toxins is charybdotoxin (ChTX). ChTX is a thirty-seven amino acid peptide isolated from venom of the old world scorpion *Leiurus quinquetriatus* var. *hebraeus*. Originally described as an inhibitor of the high-conductance, $Ca^{+2}$-activated K (Maxi-K) channel present in muscle and neuro-endocrine cells, ChTX was later found also to inhibit a number of different medium- and small-conductance $Ca^{+2}$-activated K-channels, as well as a voltage-dependent K-channel (K(v) 1.3). In each case, channel inhibition occurs with similar potency, in the low nanomolar range. A related toxin, iberiotoxin (IbTX), shares 68% sequence homology with ChTX and selectively blocks the Maxi-K channel. Other peptidyl inhibitors, such as limbatustoxin (LbTX) and kaliotoxin (KTX), have also been shown to possess greater selectivity for the Maxi-K channel. Other peptidyl toxins homologous to ChTX have been identified (e.g., noxiustoxin).

Potassium channels modulate a number of cellular events such as muscle contraction, neuro-endocrine secretion, frequency and duration of action potentials, electrolyte homeostasis, and resting membrane potential. These channels comprise a family of proteins that have been classified according to their biophysical and pharmacological characteristics. Inhibition of K-channels, in their role as modulators of the plasma membrane potential in human T-lymphocytes, has been postulated to play a role in eliciting immunosuppressive responses. In regulating membrane potential, K-channels play a role in the regulation of intracellular $Ca^{+2}$ homeostasis, which has been found to be important in T-cell activation.

Potassium channel agonists are small polypeptides (31 to 37 amino acids) which form compact structures kept rigid by three disulfide bridges. Use of synthetic analogs with point mutations has determined that single amino acids residues are important for receptor binding and for biological activity of K-channel toxins (Sabatier et al. (1994) *Int. J Peptide Protein Res.* 43:486–495). Moreover, a drug with high affinity for the receptor could be expected to produce irreversible blockade of synaptic transmission. When labeled with a tracer molecule, such a drug would provide a reliable way of tagging receptors to permit measurement of their number and distribution within cells and tissues. These features would have very valuable consequences for research on excitatory amino acid neurotransmission and for the development of therapeutic agents to treat central nervous system dysfunction in humans and animals. Methods for treating heart and neurological diseases by applying toxins derived from spiders have been described (U.S. Pat. No. 4,925,664).

Arthropod animals, including insects, and certain parasitic worms, use excitatory amino acids as a major chemical neurotransmitter at their neuromuscular junction and in their central nervous system. Because of the damage done by insect pests and the prevalence of parasitic worm infections in animals and humans in many countries, there is a constant need for potent and specific new pesticides and anthelmintic drugs that are non-toxic to humans, pets, and farm animals.

Many arthropods produce a mixture of insecticidal proteins referred to as venom. These toxic substances are synthesized in specialized glandular tissues, which, when directed by a stinging or piercing apparatus, are capable of paralyzing the arthropod's prey. Small, slow moving or stationary arthropods have adapted a strategy to instantaneously paralyze their prey by utilizing neurotoxic components of the venom at very low concentrations. These components or neurotoxins interfere with the function of insect nervous tissues through efficient competition for certain receptor sites. Many of these neurotoxins are polypeptides. These have been divided into different classes based on their host specificity and mode of action (Zlotkin (1991) *Phytoparasitica* 19:177–182). For example, neurotoxic peptides isolated from numerous species of scorpions have been divided into classes that affect arthropods and classes that affect mammals.

Due to a combination of problems associated with some synthetic insecticides, including toxicity, environmental hazards, and loss of efficacy due to resistance, there exists a continuing need for the development of novel means of invertebrate control, including the development of genetically engineered recombinant baculoviruses which express protein toxins capable of incapacitating the host more rapidly than the baculovirus infection per se.

Scorpion venoms have been identified as possible sources of compounds providing insecticidal properties. Two insect-selective toxins isolated from the venom of the scorpion *Leiurus quinquestriatus* and affecting sodium conductance have been reported previously (Zlotkin et al. (1985) *Arch. Biochem. and Biophysics* 240:877–87). One toxin, AaIT, induced fast excitatory contractive paralysis of fly larvae and the other, LqhIT2, induced slow depressant flaccid paralysis suggesting that these two toxins have different chemical and pharmacological properties (Zlotkin et al. (1971) *Biochimie* (Paris) 53:1073–1078). Thus, other toxins derived from scorpion venom will also have different chemical and pharmacological properties.

SUMMARY OF THE INVENTION

The present invention relates to isolated polynucleotides comprising a nucleotide sequence encoding a K-channel agonist polypeptide having at least 25 amino acids that has at least 95% identity based on the Clustal method of alignment when compared to a polypeptide selected from the group consisting of a scorpion K-channel agonist polypeptide of SEQ ID NOs:2, 4, 6, 8, 10, 12, 14, and 16. The present invention also relates to an isolated polynucleotide comprising the complement of the nucleotide sequences described above.

It is preferred that the isolated polynucleotides of the claimed invention consist of a nucleic acid sequence selected from the group consisting of SEQ ID NOs:1, 3, 5, 7, 9, 11, 13, and 15 that codes for the polypeptide selected from the group consisting of SEQ ID NOs:2, 4, 6, 8, 10, 12, 14, and 16.

The present invention relates to a chimeric gene comprising an isolated polynucleotide of the present invention operably linked to suitable regulatory sequences.

The present invention relates to an isolated host cell comprising a chimeric gene of the present invention or an isolated polynucleotide of the present invention. The host cell may be eukaryotic, such as an insect, a yeast or a plant cell, or prokaryotic, such as a bacterial cell. The present invention also relates to a virus, preferably a baculovirus, comprising an isolated polynucleotide of the present invention or a chimeric gene of the present invention.

The present invention relates to a process for producing an isolated host cell comprising a chimeric gene of the present invention or an isolated polynucleotide of the present invention, the process comprising either transforming or transfecting an isolated compatible host cell with a chimeric gene or isolated polynucleotide of the present invention.

The present invention relates to a potassium channel blocking toxin 15-1, an agitoxin 1, a leiuropeptide II, a kaliotoxin 2 precursor, a tityustoxin k alpha, a charybdotoxin, or a charybdotoxin 2 polypeptide having at least 25 amino acids and at least 95% homology based on the Clustal method of alignment compared to a polypeptide selected from the group consisting of SEQ ID NOs:2, 4, 6, 8, 10, 12, 14, and 16.

The present invention relates to a method of selecting an isolated polynucleotide that affects the level of expression of a potassium channel blocking toxin 15-1, an agitoxin 1, a leiuropeptide II, a kaliotoxin 2 precursor, a tityustoxin k alpha, a charybdotoxin, or a charybdotoxin 2 polypeptide in a host cell, the method comprising the steps of: (a) constructing an isolated polynucleotide of the present invention or an isolated chimeric gene of the present invention; (b) introducing the isolated polynucleotide or the isolated chimeric gene into a host cell; (c) measuring the level a potassium channel blocking toxin 15-1, an agitoxin 1, a leiuropeptide II, a kaliotoxin 2 precursor, a tityustoxin k alpha, a charybdotoxin, or a charybdotoxin 2 polypeptide in the host cell containing the isolated polynucleotide; and (d) comparing the level of a potassium channel blocking toxin 15-1, an agitoxin 1, a leiuropeptide II, a kaliotoxin 2 precursor, a tityustoxin k alpha, a charybdotoxin, or a charybdotoxin 2 polypeptide in the host cell containing the isolated polynucleotide with the level of a potassium channel blocking toxin 15-1, an agitoxin 1, a leiuropeptide II, a kaliotoxin 2 precursor, a tityustoxin k alpha, a charybdotoxin, or a charybdotoxin 2 polypeptide in a host cell that does not contain the isolated polynucleotide.

The present invention relates to a method of obtaining a nucleic acid fragment encoding a substantial portion of a potassium channel blocking toxin 15-1, an agitoxin 1, a leiuropeptide II, a kaliotoxin 2 precursor, a tityustoxin k alpha, a charybdotoxin, or a charybdotoxin 2 polypeptide gene, preferably a scorpion K-channel agonist polypeptide gene. comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1,3, 5, 7, 9, 11, 13, 15, and the complement of such nucleotide sequences; and amplifying a nucleic acid fragment (preferably a cDNA inserted in a cloning vector) using the oligonucleotide primer. The amplified nucleic acid fragment preferably will encode a portion of a potassium channel blocking toxin 15-1, an agitoxin 1, a leiuropeptide II, a kaliotoxin 2 precursor, a tityustoxin k alpha, a charybdotoxin, or a charybdotoxin 2 amino acid sequence.

The present invention also relates to a method of obtaining a nucleic acid fragment encoding all or a substantial portion of the amino acid sequence encoding a potassium channel blocking toxin 15-1, an agitoxin 1, a leiuropeptide II, a kaliotoxin 2 precursor, a tityustoxin k alpha, a charybdotoxin, or a charybdotoxin 2 polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

Another embodiment of the instant invention pertains to a method for expressing a gene encoding a potassium channel blocking toxin 15-1, an agitoxin 1, a leiuropeptide II, a kaliotoxin 2 precursor, a tityustoxin k alpha, a charybdotoxin, or a charybdotoxin 2 in the genome of a recombinant baculovirus in insect cell culture or in viable insects wherein said insect cells or insects have been genetically engineered to express a potassium channel blocking toxin 15-1, an agitoxin 1, a leiropeptide II, a kaliotoxin 2 precursor, a tityustoxin k alpha, a charybdotoxin, or a charybdotoxin 2.

BRIEF DESCRIPTION OF THE DRAWINGS AND SEQUENCE LISTING

The invention can be more fully understood from the following detailed description and the accompanying drawing and Sequence Listing which form a part of this application.

FIG. 1 shows a comparison of the amino acid sequence of the potassium channel blocking toxin 15-1 of the instant invention (clone 1st.pk0005.c5; SEQ ID NO:2) with the sequence of potassium channel blocking toxin 15-1 from *Leiurus quinquestriatus* (NCBI General Identifier No. 1173380; SEQ ID NO:17). The conserved cysteine residues, probably involved in intrachain disulfide bridges, are boxed in black, written in white, and indicated with asterisks (*) on the top row.

FIG. 2 shows a comparison of the amino acid sequence of the agitoxin 1 of the instant invention (clone 1st.pk0006.e4; SEQ ID NO:4) with the sequence of agitoxin 1 from *Leiurus quinquestriatus* (NCBI General Identifier No. 1173372; SEQ ID NO:18). The conserved cysteine residues, probably involved in intrachain disulfide bridges, are boxed in black. written in white, and indicated with asterisks (*) on the top row.

FIG. 3 shows a comparison of the amino acid sequences of the leiuropeptide II of the instant invention (clone 1st.pk0014.e7; SEQ ID NO:6) with the sequence of the Leiuropeptide II from *Leiurus quinquestriatus hebraeus* (NCBI General Identifier No. 1711348; SEQ ID NO:19). The conserved cysteine residues, probably involved in intrachain disulfide bridges, are boxed in black, written in white, and indicated with asterisks (*) on the top row.

FIG. 4 shows a comparison of the amino acid sequences of the kaliotoxin 2 precursor of the instant invention (clone 1st.pk0014.f8; SEQ ID NO:8) with the sequence of kaliotoxin 2 precursor from *Androctonus australis* (NCBI General Identifier No. 1173377; SEQ ID NO:20). The conserved cysteine residues, probably involved in intrachain disulfide bridges, are boxed in black. written in white, and indicated with asterisks (*) on the top row.

FIG. 5 shows a comparison of the amino acid sequences of the tityustoxin k alpha of the instant invention (clone 1st.pk0015.d2.f; SEQ ID NO:10) with the sequence of the tityustoxin k alpha from *Tityus serrulatus* (NCBI General Identifier No. 1173382; SEQ ID NO:21). The conserved cysteine residues, probably involved in intrachain disulfide bridges, are boxed in black, written in white, and indicated with asterisks (*) on the top row.

FIG. 6 shows a comparison of the amino acid sequences of the charybdotoxin of the instant invention (clone 1st.pk0011.d2; SEQ ID NO:12) with the sequence of charybdotoxin from *Leurus quinquestriatus* (NCBI General Identifier No. 464740; SEQ ID NO:22). The conserved cysteine residues, probably involved in intrachain disulfide bridges, are boxed in black, written in white, and indicated with asterisks (*) on the top row.

FIG. 7 shows a comparison of the amino acid sequences of the charybdotoxin of the instant invention (clone 1st.pk0016.c8.f; SEQ ID NO:14) with the sequence of the charybdotoxin artificial sequence (NCBI General Identifier No. 208161; SEQ ID NO:23). The conserved cysteine residues, probably involved in intrachain disulfide bridges, are boxed in black, written in white, and indicated with asterisks (*) on the top row.

FIG. 8 shows a comparison of the amino acid sequences of the charybdotoxin 2 of the instant invention (clone 1st.pk0018.e11; SEQ ID NO:16) with the sequence of the charybdotoxin 2 from *Leiurus quinquestriatus hebraeus* (NCBI General Identifier No. 1173379; SEQ ID NO:24). The conserved cysteine residues, probably involved in intrachain disulfide bridges, are boxed in black, written in white, and indicated with asterisks (*) on the top row.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Scorpion Potassium Channel Agonists

| Protein | Clone Designation | SEQ ID NO: (Nucleotide) | SEQ ID NO: (Amino Acid) |
|---|---|---|---|
| Scorpion Potassium Channel Blocking Toxin 15-1 | lst.pk0005.c5 | 1 | 2 |
| Scorpion Agitoxin 1 | lst.pk0006.e4 | 3 | 4 |
| Scorpion Leiuropeptide II | lst.pk0014.e7 | 5 | 6 |
| Scorpion Kaliotoxin 2 Precursor I | lst.pk0014.f8 | 7 | 8 |
| Scorpion Tityustoxin k Alpha | lst.pk0015.d2.f | 9 | 10 |
| Scorpion Charybdotoxin | lst.pk0011.d2 | 11 | 12 |
| Scorpion Charybdotoxin | lst.pk0016.c8.f | 13 | 14 |
| Scorpion Charybdotoxin 2 | lst.pk0018.e11 | 15 | 16 |

The Sequence Listing contains the one letter code for nucleotide sequence characters and the three letter codes for amino acids as defined in conformity with the IUPAC-IUBMB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "polynucleotide" is a nucleotide sequence such as a nucleic acid fragment. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least one of 60 contiguous nucleotides, preferably at least one of 40 contiguous nucleotides, most preferably one of at least 30 contiguous nucleotides, of the nucleic acid sequence of the SEQ ID NOs:1, 3, 5, 7, 9, 11, 13, and 15.

"NPV" stands for Nuclear Polyhedrosis Virus, a baculovirus. "Polyhedrosis" refers to any of several virus diseases of insect larvae characterized by dissolution of tissues and accumulation of polyhedral granules in the resultant fluid. "PIBs" are polyhedral inclusion bodies. "AcNPV" stands for the wild-type *Autographa californica* Nuclear Polyhedrosis Virus.

As used herein, "substantially similar" refers to nucleic acid fragments wherein changes in one or more nucleotide bases results in substitution of one or more amino acids, but do not affect the functional properties of the polypeptide encoded by the polynucleotide sequence. "Substantially similar" also refers to modifications of the nucleic acid fragments of the instant invention such as deletion or insertion of one or more nucleotides that do not substantially affect the functional properties of the resulting protein molecule. It is therefore understood that the invention encompasses more than the specific exemplary sequences.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are at least about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least about 50 amino acids, preferably at least about 100 amino acids, more preferably at least about 150 amino acids, still more preferably at least about 200 amino acids, and most preferably at least about 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in a variety of cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, DNA fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Functional RNA" refers to sense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Overexpression" refers to the production of a gene product in transgenic organisms that exceeds levels of production in normal or non-transformed organisms.

"Altered levels" refers to the production of gene product(s) in transgenic organisms in amounts or proportions that differ from that of normal or non-transformed organisms.

A "signal sequence" is an amino acid sequence that is covalently linked to an amino acid sequence representing a mature protein. The signal sequence directs the protein to the secretory system (Chrispeels (1991) *Ann. Rev. Plant Phys. Plant Mol. Biol.* 42:21–53). "Mature" protein refers to a post-translationally processed polypeptide; i.e., one from which any pre- or pro-peptides, including signal sequences, present in the primary translation product have been removed. "Precursor" protein refers to the primary product of translation of mRNA; i.e., with pre- and pro-peptides still present. Pre- and pro-peptides may be but are not limited to intracellular localization signals.

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (*London*) 327:70–73; U.S. Pat. No. 4,945,050, incorporated herein by reference).

It is understood that "an insect cell" refers to one or more insect cells maintained in vitro as well as one or more cells found in an intact, living insect.

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

Nucleic acid fragments encoding at least a portion of several scorpion potassium channel agonists have been isolated and identified by comparison of cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other arthropod species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other potassium channel blocking toxin 15-1, agitoxin 1, leiuropeptide II, kaliotoxin 2, tityustoxin k alpha, chrybdotoxin or charybdotoxin 2, either as cDNAs or genomic DNAs, could be isolated directly by using all or a portion of the instant nucleic acid fragments as DNA hybridization probes to screen libraries from any desired arthropod employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency. In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the MRNA precursor encoding arthropod genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least one of 60 (preferably one of at least 40, most preferably one of at least 30) contiguous nucleotides derived from a nucleotide sequence selected from the group consisting of SEQ ID NOs:1, 3, 5, 7, 9, 11, 13, 15 and the complement of such nucleotide sequences may be used in such methods to obtain a nucleic acid fragment encoding a substantial portion of an amino acid sequence of a polypeptide such as Scorpion Potassium Channel Blocking Toxin 15-1 protein. The present invention relates to a method of obtaining a nucleic acid fragment encoding a polypeptide (such as Potassium Channel Blocking Toxin 15-1 protein, an Agitoxin 1, a Leiuropeptide II, a Kaliotoxin 2 Precursor I, a Tityustoxin k Alpha, or a Charybdotoxin), comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 3, 5, 7, 9, 11, 13, 15 and the complement of such nucleotide sequences; and amplifying a nucleic acid fragment (preferably a cDNA inserted in a cloning vector) using the oligonucleotide primer. The amplified nucleic acid fragment preferably will encode a portion of a polypeptide (such as Potassium Channel Blocking Toxin 15-1 protein, an Agitoxin 1, a Leiuropeptide II, a Kaliotoxin 2 Precursor I, a Tityustoxin k Alpha, or a Charybdotoxin).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

The nucleic acid fragments of the instant invention may be used to create transgenic plants in which the disclosed K-channel agonists are expressed. This would be useful as a means for controlling insect pests by producing plants that are more insect-tolerant than the naturally occurring variety.

Expression in plants of the proteins of the instant invention may be accomplished by 35 first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, LC-MS, or phenotypic analysis.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded K-channel agonist. An example of a vector for high level expression of the instant polypeptides in a bacterial host is provided (Example 6).

Insecticidal baculoviruses have great potential to provide an environmentally benign method for agricultural insect pest control. However, improvements to efficacy are required in order to make these agents competitive with current chemical pest control agents. One approach for making such improvements is through genetic alteration of the virus. For instance, it may be possible to modify the viral genome in order to improve the host range of the virus, to increase the environmental stability and persistence of the virus, or to improve the infectivity and transmission of the virus. In addition, improving the rate at which the virus acts to compromise the infected insect would significantly enhance the attractiveness of insecticidal baculoviruses as adjuncts or replacements for chemical pest control agents.

One method for increasing the speed with which the virus affects its insect host is to introduce into the baculovirus foreign genes that encode proteins that are toxic to the insect wherein death or incapacitation of the insect is no longer dependent solely on the course of the viral infection, but instead is aided by the accumulation of toxic levels of the foreign protein. The results are insecticidal recombinant baculoviruses.

Recombinant baculoviruses expressing the instant K-channel agonists (or portions thereof) may be prepared by protocols now known to the art (e.g., Tomalski et al., U.S. Pat. No. 5,266,317, exemplifying neurotoxins from the insect-parasitic mites; McCutchen et al. (1991) *Bio/Technology* 9:848–852; Maeda et al. (1991) *Virology* 184:777–780, illustrating construction of a recombinant baculovirus expressing AaIT; also see O'Reilly et al. (1992) *Baculovirus Expression Vectors: A Laboratory Manual*, W. H. Freeman and Company, New York; King and Possee (1992) *The Baculovirus Expression System*, Chapman and Hall, London; U.S. Pat. No. 4,745,051). These methods of gene expression provide economical preparation of foreign proteins in a eukaryotic expression vector system, in many instances yielding proteins that have achieved their proper tertiary conformation and formed the proper disulfide bridges necessary for activity.

Commonly, the introduction of heterologous genes into the baculovirus genome occurs by homologous recombination between viral genomic DNA and a suitable "transfer vector" containing the heterologous gene of interest. These transfer vectors are generally plasmid DNAs that are capable of autonomous replication in bacterial hosts, affording facile genetic manipulation. Baculovirus transfer vectors also contain a genetic cassette comprising a region of the viral genome that has been modified to include the following features (listed in the 5' to 3' direction): 1) viral DNA comprising the 5' region of a non-essential genomic region; 2) a viral promoter; 3) one or more DNA sequences encoding restriction enzyme sites facilitating insertion of heterologous DNA sequences; 4) a transcriptional termination sequence; and 5) viral DNA comprising the 3' region of a non-essential genomic region. A heterologous gene of interest is inserted into the transfer vector at the restriction site downstream of the viral promoter. The resulting cassette comprises a chimeric gene wherein the heterologous gene is under the transcriptional control of the viral promoter and transcription termination sequences present on the transfer vector. Moreover, this chimeric gene is flanked by viral DNA sequences that facilitate homologous recombination at a non-essential region of the viral genome. Recombinant viruses are created by co-transfecting insect cells that are capable of supporting viral replication with viral genomic DNA and the recombinant transfer vector. Homologous recombination between the flanking viral DNA sequences present on the transfer vector and the homologous sequences on the viral genomic DNA takes place and results in insertion of the chimeric gene into a region of the viral genome that does not disrupt an essential viral function. The infectious recombinant virion consists of the recombined genomic DNA, referred to as the baculovirus expression vector, surrounded by a protein coat.

In a preferred embodiment, the non-essential region of the viral genome that is present on the transfer vector comprises the region of the viral DNA responsible for polyhedrin production. Most preferred is a transfer vector that contains the entire polyhedrin gene between the flanking sequences that are involved in homologous recombination. Recombination with genomic DNA from viruses that are defective in polyhedrin production (due to a defect in the genomic copy of the polyhedrin gene) will result in restoration of the polyhedrin-positive phenotype. This strategy facilitates identification and selection of recombinant viruses.

In another embodiment, baculoviral genomic DNA can be directly modified by introduction of a unique restriction enzyme recognition sequence into a non-essential region of the viral genome. A chimeric gene comprising the heterologous gene to be expressed by the recombinant virus and operably linked to regulatory sequences capable of directing gene expression in baculovirus-infected insect cells, can be constructed and inserted directly into the viral genome at the unique restriction site. This strategy eliminates both the need for construction of transfer vectors and reliance on homologous recombination for generation of recombinant viruses. This technology is described by Ernst et al. (Ernst et al. (1994) *Nuc. Acid Res*. 22: 2855–2856), and in WO 94/28114.

Recombinant baculovirus expression vectors suitable for delivering genetically encoded insect-specific neurotoxins require optimal toxin gene expression for maximum efficacy. A number of strategies can be used by the skilled artisan to design and prepare recombinant baculoviruses wherein toxin gene expression results in sufficient quantities of toxin produced at appropriate times during infection in a functional form and available for binding to target cells within the insect host.

The isolated toxin gene fragment may be digested with appropriate enzymes and may be inserted into the pTZ-18R plasmid (Pharmacia, Piscataway, N.J.) at the multiple cloning site using standard molecular cloning techniques. Following transformation of *E. coli* DH5αMCR, isolated colonies may be chosen and plasmid DNA prepared. Positive clones will be identified and sequenced with the commercially available forward and reverse primers.

*Spodoptera frugiperda* cells (Sf-9) may be propagated in ExCell® 401 media (JRH Biosciences, Lenexa, Kans.) supplemented with 3.0% fetal bovine serum. Lipofectin® (50 μL at 0.1 mg/mL, Gibco/BRL) may be added to a 50 μL aliquot of the transfer vector containing the toxin gene of interest (500 ng) and linearized polyhedrin-negative AcNPV (2.5 μg, Baculogold® viral DNA, Pharmigen, San Diego, Calif.). Sf-9 cells (approximate 50% monolayer) may be co-transfected with the viral DNA/transfer vector solution. The supernatant fluid from the co-transfection experiment may be collected at 5 days post-transfection and recombinant viruses may be isolated employing standard plaque purification protocols, wherein only polyhedrin-positive plaques will be selected (Granados and Lawler (1981) *Virology*, 108, 297–308).

To propagate the recombinant virus of interest, isolated plaques may be picked and suspended in 500 μL of ExCell® media supplemented with 2.5% fetal bovine serum. Sf-9 cells in 35 mM petri dishes (50% monolayer) may be inoculated with 100 μL. of the viral suspension, and supernatant fluids collected at 5 days post infection. These supernatant fluids will be used to inoculate cultures for large scale propagation of recombinant viruses Expression of the encoded toxin gene by the recombinant baculovirus will be confirmed using a bioassay. LCMS, or antibodies. The presence of toxin activity in the recombinant viruses will be monitored in vivo. These assays involve comparison of biological activity of recombinant viruses to wild-type. Third instar larvae of *H. virescens* are infected orally by consumption of diet that contains test and control viruses and the larvae monitored for behavioral changes and mortality.

Isolated plugs of a standard insect diet are inoculated with approximately 5000 PIBs of each virus. Individual larvae. that have not fed for 12 h prior to beginning of the bioassay are allowed to consume the diet for 24 h. The larvae are transferred to individual wells in a diet tray and monitored for symptoms and mortality on a daily basis (Zlotkin et al. (1991) *Biochimie* (Paris) 53:1073–1078).

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries: Isolation and Sequencing of cDNA Clones cDNA libraries representing mRNAs from Leurus scorpion telson tissues were prepared. cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) Science 252:1651–1656). The resulting ESTs are analyzed using a Perkin Elmer Model 377 fluorescent sequencer.

Example 2

Identification of cDNA Clones

ESTs encoding K-channel agonsists were identified by conducting BLAST (Basic Local Alignment Search Tool; Altschul et al. (1993) *J. Mol. Biol.* 215:403–410 searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:200–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding K-Channel Agonists

The BLASTX search using the EST sequences from clones listed in Table 3 revealed similarity of the polypeptides encoded by the cDNAs to K-channel agonists from several species. Shown in Table 3 are the organism with the closest art, the NCBI General Identifier No. of the protein with closest homology, and the BLAST results for individual ESTs:

TABLE 3

BLAST Results for Sequences Encoding Polypeptides Homologous to K-Channel Agonists

| Clone | Organism | NCBI General Identifier No. | BLAST pLog Score |
|---|---|---|---|
| lst.pk0005.c5 | *Leiurus quinquestriatus* | 1173380 | 16.00 |
| lst.pk0006.e4 | *Leiurus quinquestriatus* | 1173372 | 5.40 |
| lst.pk0014.e7 | *Leiurus quinquestriatus* | 1711348 | 14.10 |
| lst.pk0014.f8 | *Androctonus australis* | 1173377 | 28.00 |
| lst.pk0015.d2.f | *Tityus serrulatus* | 1173382 | 5.15 |
| lst.pk0011.d2 | *Leiurus quinquestriatus* | 464740 | 16.70 |
| lst.pk0016.c8.f | artificial sequence | 208161 | 6.00 |
| lst.pk0018.e11 | *Leiurus quinquestriatus* | 1173379 | 12.22 |

Most of the amino acid sequences deduced from the clones listed above contain a portion or an entire signal sequence and a mature protein. Table 4 lists the amino acids included in the signal sequences and the amino acids included in the mature protein.

TABLE 4

Location of the Signal Sequence and Mature Protein in the Amino Acid Sequences Deduced From the Nucleotide Sequences of cDNA Clones Encoding Polypeptides Homologous to K-Channel Agonists

| Clone | Signal Sequence | Mature Protein |
|---|---|---|
| lst.pk0005.c5 | 1–22 | 23–58 |
| lst.pk0006.e4 | 1–4 | 5–59 |
| lst.pk0014.e7 | — | 1–29 |
| lst.pk0014.f8 | 1–22 | 23–59 |
| lst.pk0015.d2.f | — | 1–37 |
| lst.pk0011.d2 | 1–13 | 14–50 |
| lst.pk0016.c8.f | 1–5 | 6–45 |
| lst.pk0018.e11 | 1–22 | 23–59 |

FIG. 1 presents an alignment of the amino acid sequences set forth in SEQ ID NO:2 and the *Leiurus quinquestriatus* sequence (SEQ ID NO:17). FIG. 2 presents an alignment of the amino acid sequences set forth in SEQ ID NO:4 and the *Leurus quinquestriatus* sequence (SEQ ID NO:18). FIG. 3 presents an alignment of the amino acid sequences set forth in SEQ ID NO:6 and the *Leiurus quinquestriatus hebraeus* sequence (SEQ ID NO:19). FIG. 4 presents an alignment of the amino acid sequences set forth in SEQ ID NO:8 and the *Androctonus australis* sequence (SEQ ID NO:20). FIG. 5 presents an alignment of the amino acid sequences set forth in SEQ ID NO:10 and the *Tityus serrulatus* sequence (SEQ ID NO:21). FIG. 6 presents an alignment of the amino acid sequences set forth in SEQ ID NO:12 and the *Leiurus quinquestriatus* sequence (SEQ ID NO:22). FIG. 7 presents an alignment of the amino acid sequences set forth in SEQ ID NO:14 and the artificial sequence (SEQ ID NO:23). FIG. 8 presents an alignment of the amino acid sequences set forth in SEQ ID NO:16 and the *Leiurus quinquestriatus hebraeus* sequence (SEQ ID NO:24).

The data in Table 5 represents a calculation of the percent identity of the amino acid sequences set forth in SEQ ID NOs:2, 4, 6, 8, 10, 12, 14 and 16 and the sequences in the NCBI database (SEQ ID NOs:17, 18, 19, 20, 21, 22, 23 and 24).

TABLE 5

Percent Identity of Amino Acid Sequences Deduced From the Nucleotide Sequences of cDNA Clones Encoding Polypeptides Homologous to K-Channel Agonists

| SEQ ID NO. | NCBI General Identifier No. | Percent Identity |
|---|---|---|
| 2 | 1173380 | 80.6 |
| 4 | 1173372 | 42.1 |
| 6 | 1711348 | 93.1 |
| 8 | 1173377 | 84.7 |
| 10 | 1173382 | 40.5 |
| 12 | 464740 | 81.1 |
| 14 | 208161 | 37.8 |
| 16 | 1173379 | 64.9 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the instant nucleic acid fragments encode eight distinct, full-length, scorpion potassium channel agonists: a potassium channel blocking toxin 15-1 with its entire signal sequence, an agitoxin 1 with partial signal sequence, a leiuropeptide II, a kaliotoxin 2 precursor with the entire signal sequence, a tityustoxin k alpha, two charybdotoxins, one of which has partial signal sequence, and a charybdotoxin 2 with its entire signal sequence.

Example 4

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (Nco I or Sma I) can be incorporated into the oligonucleotides to provide proper orientation of the DNA fragment when inserted into the digested vector pML103 as described below. Amplification is then performed in a standard PCR. The amplified DNA is then digested with restriction enzymes Nco I and Sma I and fractionated on an agarose gel. The appropriate band can be isolated from the gel and combined with a 4.9 kb Nco I-Sma I fragment of the plasmid pML103. Plasmid pML103 has been deposited under the terns of the Budapest Treaty at ATCC (American Type Culture Collection, 10801 University Blvd., Manassas, Va. 20110-2209), and bears accession number ATCC 97366. The DNA segment from pML103 contains a 1.05 kb Sal I-Nco I promoter fragment of the maize 27 kD zein gene and a 0.96 kb Sma I-Sal I fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al., (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from cauliflower mosaic virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al., (1990) *Bio/Technology* 8:833–839).

Example 5

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from cauliflower mosaic virus (Odell et al. (1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL $CaCl_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (1986) *J. Mol. Biol.* 189:1 13–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Example 7

Expression of Chimeric Genes in Insect Cells

The cDNAs encoding the instant polypeptides may be introduced into the baculovirus genome itself. For this purpose the cDNAs may be placed under the control of the polyhedron promoter, the IE1 promoter, or any other one of the baculovirus promoters. The cDNA, together with appropriate leader sequences is then inserted into a baculovirus transfer vector using standard molecular cloning techniques. Following transformation of *E. coli* DH5α, isolated colonies are chosen and plasmid DNA is prepared and is analyzed by restriction enzyme analysis. Colonies containing the appropriate fragment are isolated, propagated, and plasmid DNA is prepared for cotransfection.

*Spodoptera frugiperda* cells (Sf-9) are propagated in ExCell® 401 media (JRH Biosciences, Lenexa, Kans.) supplemented with 3.0% fetal bovine serum. Lipofectin® (50 μL at 0.1 mg/mL, Gibco/BRL) is added to a 50 μL aliquot of the transfer vector containing the toxin gene (500 ng) and linearized polyhedrin-negative AcNPV (2.5 μg, Baculogold® viral DNA, Pharmigen, San Diego, Calif.). Sf-9 cells (approximate 50% monolayer) are co-transfected with the viral DNA/transfer vector solution. The supernatant fluid from the co-transfection experiment is collected at 5 days post-transfection and recombinant viruses are isolated employing standard plaque purification protocols, wherein only polyhedrin-positive plaques are selected (O'Reilly et al. (1992), *Baculovirus Expression Vectors: A Laboratory Manual*, W. H. Freeman and Company, New York.). Sf-9 cells in 35 mM petri dishes (50% monolayer) are inoculated with 100 μL of a serial dilution of the viral suspension, and supernatant fluids are collected at 5 days post infection. In order to prepare larger quantities of virus for characterization, these supernatant fluids are used to inoculate larger tissue cultures for large scale propagation of recombinant viruses. Expression of the instant polypeptides encoded by the recombinant baculovirus is confirmed by bioassay.

Various modifications of the invention in addition to those shown and described herein will be apparent to those skilled in the art from the foregoing description. Such modifications are also intended to fall within the scope of the appended claims.

The disclosure of each reference set forth above is incorporated herein by reference in its entirety.

What is claimed is:

1. An isolated polynucleotide comprising a) a nucleotide sequence encoding a potassium channel agonist having at least 95% sequence identity, based on the Clustal method of alignment, when compared to a polypeptide of SEQ ID NO:14; or b) a complement of the nucleotide sequence of a), wherein the complement and the nucleotide sequence have the same number of nucleotides and are 100% complementary.

2. The polynucleotide of claim 1 wherein the amino acid sequence of the polypeptide comprises SEQ ID NO:14.

3. The polynucleotide of claim 1, wherein the polynucleotide comprises SEQ ID NO:13.

4. An isolated polynucleotide comprising a) a nucleotide sequence encoding a potassium channel agonist having at least 95% sequence identity, based on the Clustal method of alignment, when compared to amino acids 6–45 of SEQ ID NO:14; or b) a complement of the nucleotide sequence of a), wherein the complement and the nucleotide sequence have the same number of nucleotides and are 100% complementary.

5. The polynucleotide of claim 4 wherein the amino acid sequence of the polypeptide comprises amino acids 6–45 of SEQ ID NO:14.

6. A recombinant DNA construct comprising the polynucleotide of claim 1 or claim 4 operably linked to at least one regulatory sequence.

7. A transgenic cell comprising the recombinant DNA construct of claim 6 wherein the cell is selected from the group consisting of an insect cell, a yeast cell, a plant cell, or a bacterial cell.

8. A virus comprising the recombinant DNA construct of claim 6.

9. A method for transforming a cell comprising introducing into a cell the polynucleotide of claim 1 or claim 4 wherein the cell is selected from the group consisting of an insect cell, a yeast cell, a plant cell, or a bacterial cell.

10. A vector comprising the polynucleotide of claim 1 or claim 4.

11. An isolated polynucleotide that (a) comprises at least 75 contiguous nucleotides and (b) remains hybridized with the isolated polynucleotide of claim 1 under a wash condition of 0.1×SSC, 0.1% SDS, and 65° C.

* * * * *

SEQUENCE LISTING

```
<160> NUMBER OF SEQ ID NOS: 24

<210> SEQ ID NO 1
<211> LENGTH: 177
<212> TYPE: DNA
<213> ORGANISM: Leiurus quinquestriatus
```

-continued

<400> SEQUENCE: 1
atgaaaattt tgtctgttct tttgatagct ttcattatct gttcaataaa catttgtagt 60
gaagctggac tcatagacgt aagatgtttt gcatctcgtg aatgttggga agcttgcaga 120
aaagtaacag gatcgggaca aggaaaatgc cagaataatc aatgtcgctg ctattaa 177

<210> SEQ ID NO 2
<211> LENGTH: 58
<212> TYPE: PRT
<213> ORGANISM: Leiurus quinquestriatus

<400> SEQUENCE: 2

Met Lys Ile Leu Ser Val Leu Leu Ile Ala Phe Ile Ile Cys Ser Ile
1 5 10 15

Asn Ile Cys Ser Glu Ala Gly Leu Ile Asp Val Arg Cys Phe Ala Ser
20 25 30

Arg Glu Cys Trp Glu Ala Cys Arg Lys Val Thr Gly Ser Gly Gln Gly
35 40 45

Lys Cys Gln Asn Asn Gln Cys Arg Cys Tyr
50 55

<210> SEQ ID NO 3
<211> LENGTH: 120
<212> TYPE: DNA
<213> ORGANISM: Leiurus quinquestriatus
<220> FEATURE:
<221> NAME/KEY: unsure
<222> LOCATION: (112)
<223> OTHER INFORMATION: n = A, C, G, or T
<220> FEATURE:
<221> NAME/KEY: unsure
<222> LOCATION: (114)
<223> OTHER INFORMATION: n = A, C, G, or T

<400> SEQUENCE: 3
tttatcaatt cgaatgtgga agctgcttgc ggtcctggat gccgaagttc atgtcaacaa 60
agtggcaaca gtggaggaaa gtgtattaat ggaagatgcc actgctatcc angnaagtaa 120

<210> SEQ ID NO 4
<211> LENGTH: 39
<212> TYPE: PRT
<213> ORGANISM: Leiurus quinquestriatus
<220> FEATURE:
<221> NAME/KEY: UNSURE
<222> LOCATION: (38)
<223> OTHER INFORMATION: Xaa = ANY AMINO ACID

<400> SEQUENCE: 4

Phe Ile Asn Ser Asn Val Glu Ala Ala Cys Gly Pro Gly Cys Arg Ser
1 5 10 15

Ser Cys Gln Gln Ser Gly Asn Ser Gly Gly Lys Cys Ile Asn Gly Arg
20 25 30

Cys His Cys Tyr Pro Xaa Lys
35

<210> SEQ ID NO 5
<211> LENGTH: 90
<212> TYPE: DNA
<213> ORGANISM: Leiurus quinquestriatus -continued

<400> SEQUENCE: 5
gtttcctgtg aagactgccc tgagcactgc tccacacaga aagcccgagc aaaatgtgat 60
aatgacaaat gcgtatgtga atctatatga 90

<210> SEQ ID NO 6
<211> LENGTH: 29
<212> TYPE: PRT
<213> ORGANISM: Leiurus quinquestriatus

<400> SEQUENCE: 6

Val Ser Cys Glu Asp Cys Pro Glu His Cys Ser Thr Gln Lys Ala Arg
1 5 10 15

Ala Lys Cys Asp Asn Asp Lys Cys Val Cys Glu Ser Ile
20 25

<210> SEQ ID NO 7
<211> LENGTH: 180
<212> TYPE: DNA
<213> ORGANISM: Leiurus quinquestriatus

<400> SEQUENCE: 7
atgaaggtgt ttttcgcagt tttaataact ctcttcgttt gttcaatgat tattggaatt 60
aatgcagtgg gaattccagt gtcatgtata cattctcgtc aatgttggga accatgtaag 120
aaagctggaa tgagatttgg aaaatgcatg aatcgcaaat gcgattgcac accaaagtga 180

<210> SEQ ID NO 8
<211> LENGTH: 59
<212> TYPE: PRT
<213> ORGANISM: Leiurus quinquestriatus

<400> SEQUENCE: 8

Met Lys Val Phe Phe Ala Val Leu Ile Thr Leu Phe Val Cys Ser Met
1 5 10 15

Ile Ile Gly Ile Asn Ala Val Gly Ile Pro Val Ser Cys Ile His Ser
20 25 30

Arg Gln Cys Trp Glu Pro Cys Lys Lys Ala Gly Met Arg Phe Gly Lys
35 40 45

Cys Met Asn Arg Lys Cys Asp Cys Thr Pro Lys
50 55

<210> SEQ ID NO 9
<211> LENGTH: 114
<212> TYPE: DNA
<213> ORGANISM: Leiurus quinquestriatus

<400> SEQUENCE: 9
atacatacaa atgtgccgtg caagaattct ggacaatgtc gtccagtttg cataaaaaga 60
gtaaataata atagcggaaa gtgtggtaat gacaaatgta tttgttatcc ataa 114

<210> SEQ ID NO 10
<211> LENGTH: 37
<212> TYPE: PRT
<213> ORGANISM: Leiurus quinquestriatus -continued

<400> SEQUENCE: 10

```
Ile His Thr Asn Val Pro Cys Lys Asn Ser Gly Gln Cys Arg Pro Val
  1               5                  10                  15

Cys Ile Lys Arg Val Asn Asn Asn Ser Gly Lys Cys Gly Asn Asp Lys
             20                  25                  30

Cys Ile Cys Tyr Pro
         35
```

<210> SEQ ID NO 11
<211> LENGTH: 150
<212> TYPE: DNA
<213> ORGANISM: Leiurus quinquestriatus

<400> SEQUENCE: 11

```
ctctcatcca tttgttcaat agtaggttgg agtgaagctc aatttacgga tgtaagttgt     60

actacatcta aagaatgttg gtcggtttgt gagacattgt ataagaccac cagaggaaag    120

tgcatgaatt ggaaatgccg ctgttattcg                                     150
```

<210> SEQ ID NO 12
<211> LENGTH: 50
<212> TYPE: PRT
<213> ORGANISM: Leiurus quinquestriatus

<400> SEQUENCE: 12

```
Leu Ser Ser Ile Cys Ser Ile Val Gly Trp Ser Glu Ala Gln Phe Thr
  1               5                  10                  15

Asp Val Ser Cys Thr Thr Ser Lys Glu Cys Trp Ser Val Cys Glu Thr
             20                  25                  30

Leu Tyr Lys Thr Thr Arg Gly Lys Cys Met Asn Trp Lys Cys Arg Cys
         35                  40                  45

Tyr Ser
     50
```

<210> SEQ ID NO 13
<211> LENGTH: 138
<212> TYPE: DNA
<213> ORGANISM: Leiurus quinquestriatus

<400> SEQUENCE: 13

```
atgatgattt tctgccaagg ccagaaaaaa ataaattatc gatgtaataa tagcggtgag     60

tgtattccac attgcatcag aatatataac accagagcag caaagtgtat taataaaaca    120

tgcaattgtt atccatga                                                   138
```

<210> SEQ ID NO 14
<211> LENGTH: 45
<212> TYPE: PRT
<213> ORGANISM: Leiurus quinquestriatus

<400> SEQUENCE: 14

```
Met Met Ile Phe Cys Gln Gly Gln Lys Lys Ile Asn Tyr Arg Cys Asn
  1               5                  10                  15

Asn Ser Gly Glu Cys Ile Pro His Cys Ile Arg Ile Tyr Asn Thr Arg
             20                  25                  30

Ala Ala Lys Cys Ile Asn Lys Thr Cys Asn Cys Tyr Pro
         35                  40                  45
```

-continued

<210> SEQ ID NO 15
<211> LENGTH: 180
<212> TYPE: DNA
<213> ORGANISM: Leiurus quinquestriatus

<400> SEQUENCE: 15

```
atgaaaattt tatcagctct gctactagct ctcatcattt gttcaatagt aggttggagt     60

acagctcaat ttacacaagt aagttgcagt gcatctgatc aatgttggtt ggtttgtcaa    120

aacttgtata aaacactcaa tgcaaagtgt atgaataata aatgccgctg ttattcgtaa    180
```

<210> SEQ ID NO 16
<211> LENGTH: 59
<212> TYPE: PRT
<213> ORGANISM: Leiurus quinquestriatus

<400> SEQUENCE: 16

```
Met Lys Ile Leu Ser Ala Leu Leu Leu Ala Leu Ile Ile Cys Ser Ile
  1               5                  10                  15

Val Gly Trp Ser Thr Ala Gln Phe Thr Gln Val Ser Cys Ser Ala Ser
             20                  25                  30

Asp Gln Cys Trp Leu Val Cys Gln Asn Leu Tyr Lys Thr Leu Asn Ala
         35                  40                  45

Lys Cys Met Asn Asn Lys Cys Arg Cys Tyr Ser
     50                  55
```

<210> SEQ ID NO 17
<211> LENGTH: 36
<212> TYPE: PRT
<213> ORGANISM: Leiurus quinquestriatus

<400> SEQUENCE: 17

```
Gly Leu Ile Asp Val Arg Cys Tyr Asp Ser Arg Gln Cys Trp Ile Ala
  1               5                  10                  15

Cys Lys Lys Val Thr Gly Ser Thr Gln Gly Lys Cys Gln Asn Lys Gln
             20                  25                  30

Cys Arg Cys Tyr
         35
```

<210> SEQ ID NO 18
<211> LENGTH: 38
<212> TYPE: PRT
<213> ORGANISM: Leiurus quinquestriatus

<400> SEQUENCE: 18

```
Gly Val Pro Ile Asn Val Lys Cys Thr Gly Ser Pro Gln Cys Leu Lys
  1               5                  10                  15

Pro Cys Lys Asp Ala Gly Met Arg Phe Gly Lys Cys Ile Asn Gly Lys
             20                  25                  30

Cys His Cys Thr Pro Lys
         35
```

<210> SEQ ID NO 19
<211> LENGTH: 29
<212> TYPE: PRT
<213> ORGANISM: Leiurus quinquestriatus -continued

<400> SEQUENCE: 19

```
Val Ser Cys Glu Asp Cys Pro Asp His Cys Ser Thr Gln Lys Ala Arg
  1               5                  10                  15

Ala Lys Cys Asp Asn Asp Lys Cys Val Cys Glu Pro Ile
             20                  25
```

<210> SEQ ID NO 20
<211> LENGTH: 59
<212> TYPE: PRT
<213> ORGANISM: Androctonus australis

<400> SEQUENCE: 20

```
Met Lys Val Phe Ser Ala Val Leu Ile Ile Leu Phe Val Cys Ser Met
  1               5                  10                  15

Ile Ile Gly Ile Asn Ala Val Arg Ile Pro Val Ser Cys Lys His Ser
             20                  25                  30

Gly Gln Cys Leu Lys Pro Cys Lys Asp Ala Gly Met Arg Phe Gly Lys
         35                  40                  45

Cys Met Asn Gly Lys Cys Asp Cys Thr Pro Lys
     50                  55
```

<210> SEQ ID NO 21
<211> LENGTH: 37
<212> TYPE: PRT
<213> ORGANISM: Tityus serrulatus

<400> SEQUENCE: 21

```
Val Phe Ile Asn Ala Lys Cys Arg Gly Ser Pro Glu Cys Leu Pro Lys
  1               5                  10                  15

Cys Lys Glu Ala Ile Gly Lys Ala Ala Gly Lys Cys Met Asn Gly Lys
             20                  25                  30

Cys Lys Cys Tyr Pro
         35
```

<210> SEQ ID NO 22
<211> LENGTH: 37
<212> TYPE: PRT
<213> ORGANISM: Leiurus quinquestriatus

<400> SEQUENCE: 22

```
Gln Phe Thr Asn Val Ser Cys Thr Thr Ser Lys Glu Cys Trp Ser Val
  1               5                  10                  15

Cys Gln Arg Leu His Asn Thr Ser Arg Gly Lys Cys Met Asn Lys Lys
             20                  25                  30

Cys Arg Cys Tyr Ser
         35
```

<210> SEQ ID NO 23
<211> LENGTH: 45
<212> TYPE: PRT
<213> ORGANISM: Artificial Sequence
<220> FEATURE:
<223> OTHER INFORMATION: Description of Artificial Sequence:NCBI gi
      No. 208161

-continued

```
<400> SEQUENCE: 23

Val Asp Gly Ser Ile Glu Gly Arg Gln Phe Thr Asn Val Ser Cys Thr
  1             5                  10                  15

Thr Ser Lys Glu Cys Trp Ser Val Cys Gln Arg Leu His Asn Thr Ser
             20                  25                  30

Arg Gly Lys Cys Met Asn Lys Lys Cys Arg Cys Tyr Ser
         35                  40                  45


<210> SEQ ID NO 24
<211> LENGTH: 37
<212> TYPE: PRT
<213> ORGANISM: Leiurus quinquestriatus

<400> SEQUENCE: 24

Gln Phe Thr Gln Glu Ser Cys Thr Ala Ser Asn Gln Cys Trp Ser Ile
  1             5                  10                  15

Cys Lys Arg Leu His Asn Thr Asn Arg Gly Lys Cys Met Asn Lys Lys
             20                  25                  30

Cys Arg Cys Tyr Ser
         35
```